US009750518B2

(12) United States Patent
Hocking

(10) Patent No.: US 9,750,518 B2
(45) Date of Patent: Sep. 5, 2017

(54) CATHETER APPARATUS

(75) Inventor: Gordon Donald Hocking, Chiba (JP)

(73) Assignee: ACCESS POINT TECHNOLOGIES, INC., Tokyo (JP)

( * ) Notice: Subject to any disclaimer, the term of this patent is extended or adjusted under 35 U.S.C. 154(b) by 328 days.

(21) Appl. No.: 13/698,861

(22) PCT Filed: May 25, 2011

(86) PCT No.: PCT/JP2011/002904
§ 371 (c)(1),
(2), (4) Date: Nov. 19, 2012

(87) PCT Pub. No.: WO2011/148626
PCT Pub. Date: Dec. 1, 2011

(65) Prior Publication Data
US 2013/0060276 A1 Mar. 7, 2013

(30) Foreign Application Priority Data
May 25, 2010 (JP) ................................. 2010-119350

(51) Int. Cl.
*A61M 29/00* (2006.01)
*A61B 17/221* (2006.01)
*A61B 17/22* (2006.01)
*A61F 2/01* (2006.01)

(52) U.S. Cl.
CPC .... *A61B 17/221* (2013.01); *A61B 2017/2212* (2013.01); *A61B 2017/22038* (2013.01); *A61B 2017/22084* (2013.01); *A61F 2/013* (2013.01)

(58) Field of Classification Search
CPC ........ A61B 17/221; A61B 2017/22084; A61B 2017/2212

USPC ................................. 606/200, 151, 114, 127
See application file for complete search history.

(56) References Cited

U.S. PATENT DOCUMENTS

| | | | | |
|---|---|---|---|---|
| 5,925,013 A | * | 7/1999 | Exline | 604/32 |
| 6,443,926 B1 | * | 9/2002 | Kletschka | 604/96.01 |
| 2001/0051810 A1 | * | 12/2001 | Dubrul et al. | 606/159 |
| 2002/0138094 A1 | * | 9/2002 | Borillo | 606/200 |
| 2004/0093010 A1 | * | 5/2004 | Gesswein | A61F 2/013 606/200 |

(Continued)

FOREIGN PATENT DOCUMENTS

| | | |
|---|---|---|
| JP | 10-305104 A | 11/1998 |
| JP | 2000-316986 A | 11/2000 |

(Continued)

OTHER PUBLICATIONS

PCT, "International Search Report for PCT/JP2011/002904", Jul. 12, 2011.

*Primary Examiner* — Gregory Anderson
*Assistant Examiner* — Sarah Simpson
(74) *Attorney, Agent, or Firm* — Manabu Kanesaka

(57) ABSTRACT

A catheter apparatus has a catheter that is inserted into a lumen of the human body, a branch portion which is connected to a base end portion of the catheter and is provided with an insertion hole to pass a guide wire used in inserting the catheter in the lumen of the human body, and a liquid introducing portion for introducing liquid such as a drug solution into the catheter through a tube connected to the branch portion, where at a front end of the catheter is disposed embolus trapping part for trapping an embolus inside the lumen of the human body.

13 Claims, 5 Drawing Sheets

(56) References Cited

U.S. PATENT DOCUMENTS

2007/0233174 A1* 10/2007 Hocking et al. .............. 606/200
2009/0182309 A1* 7/2009 Muffly ............... A61M 39/1011
                                                            604/535
2010/0114017 A1* 5/2010 Lenker ............. A61B 17/12118
                                                            604/96.01

FOREIGN PATENT DOCUMENTS

| JP | 2003-220062 A | 8/2003 |
| JP | 2004-097807 A | 4/2004 |
| JP | 2009-526570 A | 7/2009 |

* cited by examiner

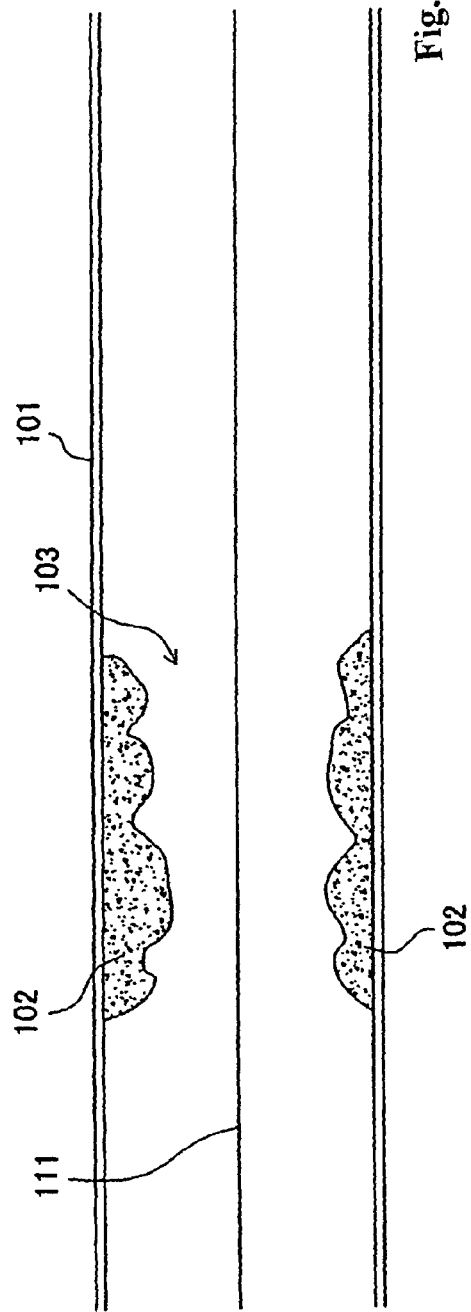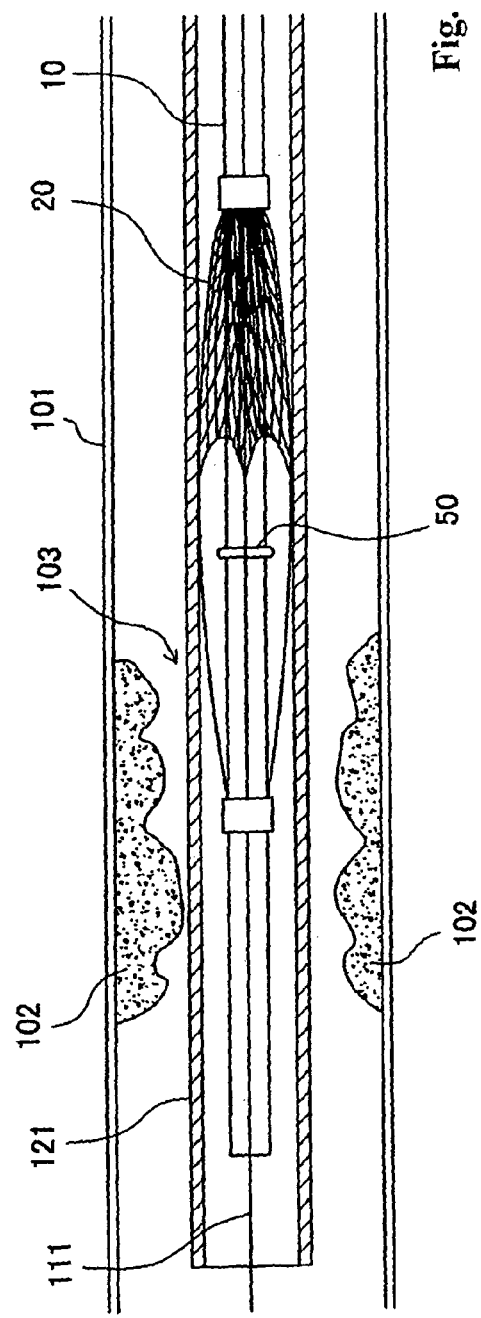

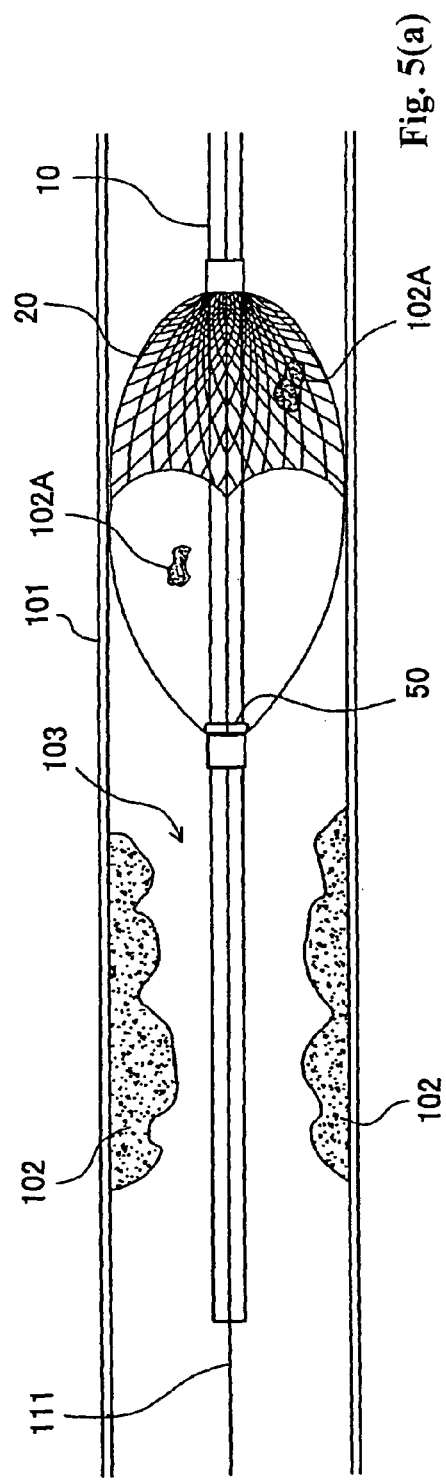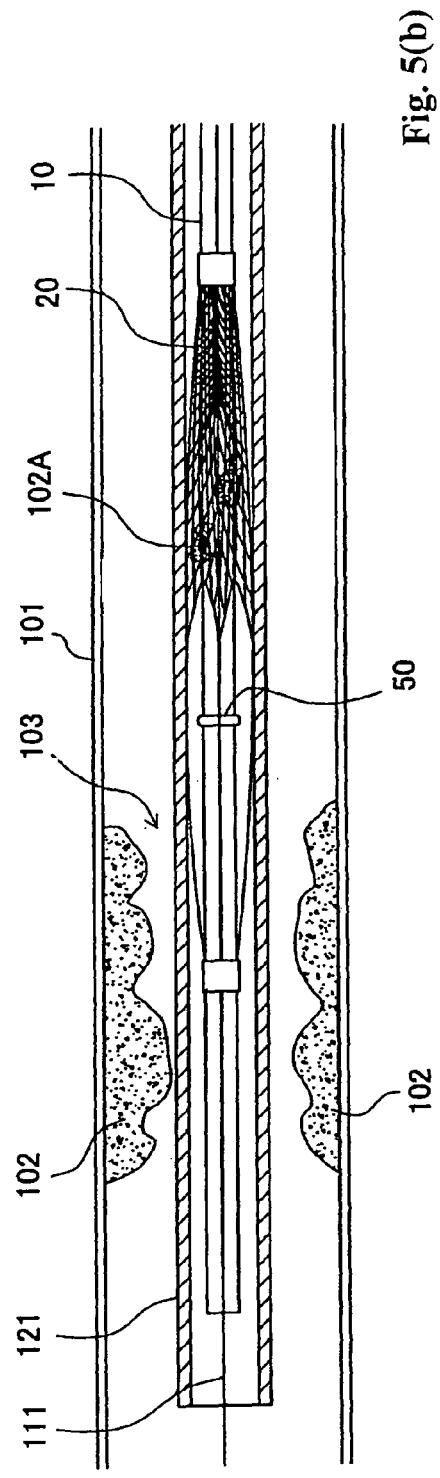

CATHETER APPARATUS

RELATED APPLICATIONS

The present application is National Phase of International Application No. PCT/JP2011/002904 filed Nov. 25, 2011, and claims priority from Japanese Application No. 2010-119350, filed May 25, 2010.

TECHNICAL FIELD

The present invention relates to a catheter apparatus capable of trapping emboli such as thrombi, while at the same performing administration of a drug, etc. and sampling of body fluid such as blood inside a lumen of the human body.

BACKGROUND ART

Thrombosis is a disease caused by blood in a blood vessel forming a clot by some reason to be a thrombus and the thrombus blocking the blood vessel and interrupting the blood stream. In sites downstream of the blocking, infarction and ischemia develop, are called cardiac infarction or cerebral infarction according to the site, and have the risk of becoming a life-threatening situation.

For example, cardiac infarction indicates conditions that the coronary artery is stenosed by thrombi, the blood flow decreases, and that the cardiac muscle becomes necrotic. In the treatment for cardiac infarction, since killing of the cardiac muscle proceeds as the ischemia time increases, and the prognosis becomes poorer as the extent of infarction increases, it is necessary to re-open (re-perfuse) the blood stream promptly.

As such a re-perfuse treatment, as well as the thrombus dissolving treatment for injecting a drug to dissolve the thrombus, there are catheter treatments (PTCA, PCI) for directly expanding the coronary artery to increase the blood flow. In recent years, with the progression of endovascular treatment techniques, methods have relatively been made ease for surgically securing the blood stream and/or removing the thrombus. More specifically, there are the blood vessel expanding treatment for expanding a stenosed lesion area by a balloon catheter, stent placement for covering a balloon with a mesh-shaped tube called the stent, inflating the balloon to fix the stent to the blood vessel, removing only the balloon to place the stent, and supporting the wall of the blood vessel from the inside, and the like.

Further, previously, such an apparatus is developed that a wire is directly passed into a stenosed site of the blood vessel, and that a basket, filter or the like provided in the wire traps an embolus (for example, see PTL 1).

CITATION LIST

Patent Literature

[PTL 1]
Japanese Patent Application Publication No. 2004-097807

SUMMARY OF INVENTION

Technical Problem

As described above, in the disease caused by a thrombus such as an embolus, unless the normal blood flow is secured early, the extent of necrosis increases, and the risk is high that the life of a patient is threatened. Accordingly, it is necessary to try re-open of the blood vessel as fast as possible. Therefore, speedy support and treatment are required such as administering a drug for dissolving the embolus while removing the thrombus such as the embolus, etc.

In view of the aforementioned circumstances, it is an object of the invention to provide a catheter apparatus capable of performing removal of an embolus such as a thrombus, administration of a drug, etc. and sampling of body fluid such as blood at the same time inside a lumen of the human body.

Solution to Problem

To solve the above-mentioned problem, the invention provides a catheter apparatus characterized by having a catheter that is inserted into a lumen of the human body, a branch portion which is connected to a base end portion of the catheter and is provided with an insertion hole to pass a guide wire used in inserting the catheter in the lumen of the human body, and liquid introducing means for introducing liquid such as a drug solution into the catheter through a tube connected to the branch portion, where at a front end of the catheter is disposed embolus trapping means for trapping an embolus inside the lumen of the human body.

Herein, it is preferable that the embolus trapping means is formed of a net member that is opened and closed in the shape of a parachute by a distance between opposite ends thereof reducing and increasing, one end of the opposite ends is tied and fixed to the catheter, and that the other end is tied to be able to slide on the surface of the catheter. Then, it is suitable that the slidable other end in the embolus trapping means is disposed on the front end side of the catheter, and is formed so that the net member opens to trap an embolus in inserting the catheter in the lumen of the human body.

Further, it is preferable that the embolus trapping means is formed of one having elasticity or shape memory characteristic of a nickel titanium wire, a titanium wire, a wire of complex material of a wire made of platinum or gold and nickel titanium alloy, a nickel wire provided with gold plating, and a wire of titanium alloy.

Furthermore, it is suitable that the branch portion is provided with the insertion hole to insert the guide wire to be inserted in the catheter, and seal means for preventing the liquid supplied through the tube from leaking from the insertion hole.

Still furthermore, it is preferable that the liquid introducing means is provided with an introduction opening to introduce the liquid into the catheter through the tube, a delivery opening to deliver body fluid such as blood to the outside through the catheter and the tube, and a switch portion provided with a valve for enabling switching of a circulation state between the catheter and the introduction opening or the delivery opening.

Then, it is suitable that the catheter and the delivery opening are communicated with each other by the switch portion, and that the body fluid such as blood is extracted from the delivery opening to the outside by applying a negative pressure to the delivery opening.

Advantageous Effects of Invention

According to the catheter apparatus of the invention, it is possible to perform removal of an embolus such as a thrombus, administration of a drug, etc. and sampling of body fluid such as blood at the same time inside a lumen of the human body.

BRIEF DESCRIPTION OF DRAWINGS

FIG. 4 contains schematic views (part 1) to explain an example of the method for using the catheter apparatus of FIG. 1.

FIG. 5 contains schematic views (part 2) to explain an example of the method for using the catheter apparatus of FIG. 1.

DESCRIPTION OF EMBODIMENTS

An Embodiment of the invention will specifically be described below with reference to drawings. In addition, in the Description, in a lumen of the human body, the upstream side (in the blood vessel, the side closer to the heart) is referred to as proximal, and the downstream side is referred to as distal. Further, in the Description, as well as a thrombus, general substances such as a fat embolus and tumor embolus for blocking the inside of a lumen are collectively referred to as an embolus.

Figure 1:
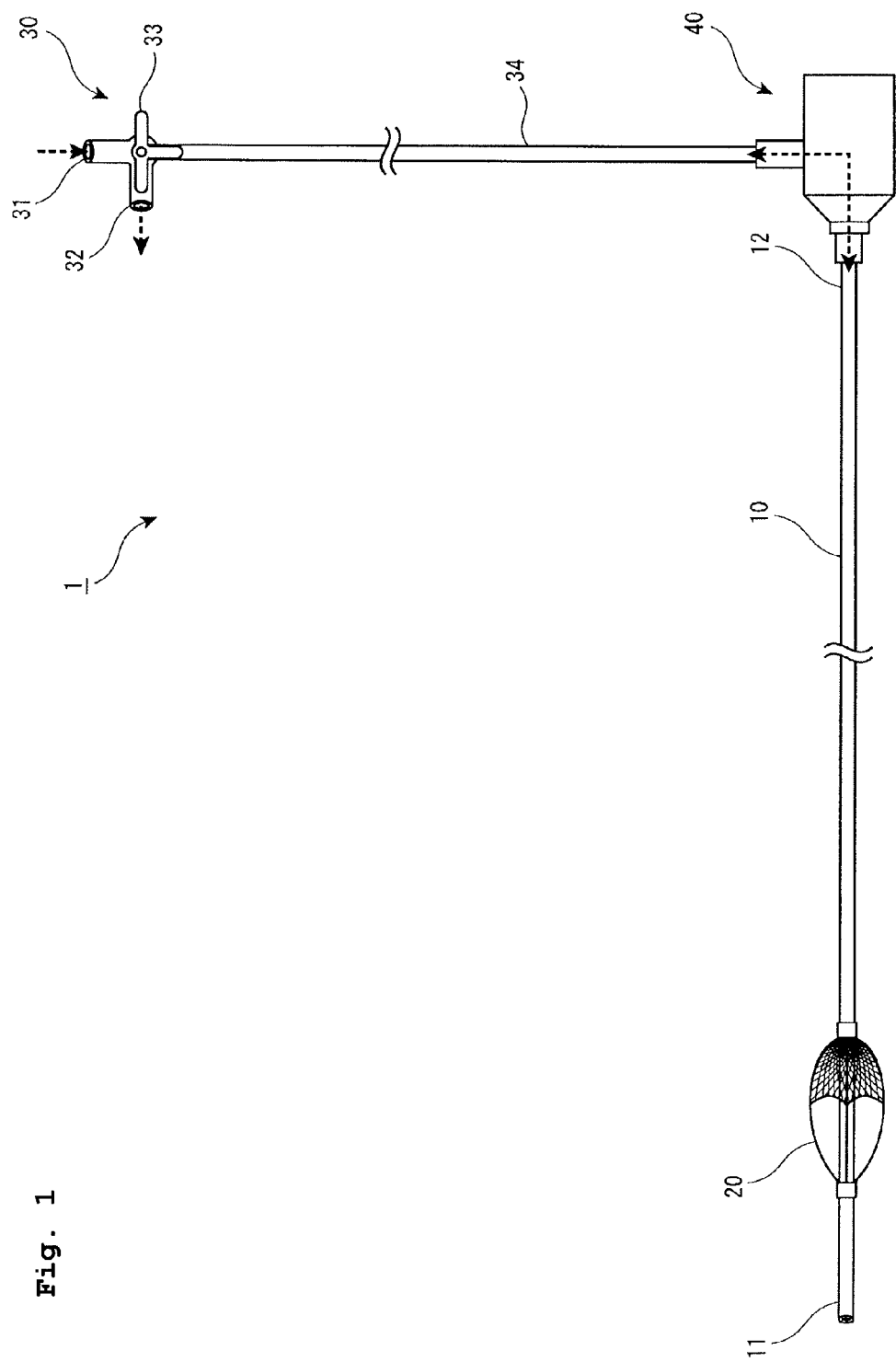
FIG. 1 is an entire schematic view of a catheter apparatus according to an Embodiment of the invention.

FIG. 1 is an entire schematic view of a catheter apparatus according to an Embodiment of the invention. As shown in the figure, the catheter apparatus 1 is comprised of a catheter 10, filter portion (embolus trapping means) 20, liquid introduction portion (liquid introducing means) and branch portion 40.

In the catheter 10, the filter portion 20 is disposed in the vicinity of a front end (proximal side) 11, while a base end (distal side) 12 is comprised of a soft hollow tube connected to the branch portion 40. The catheter apparatus 10 is inserted in a lumen inside the body of a patient together with the filter portion 20 to be used.

The filter portion 20 is comprised of a wire 21 woven in the shape of a net. It is suitable that the wire 21 is comprised of a nickel titanium wire, a titanium wire, a wire of complex material of a wire made of platinum or gold and nickel titanium alloy, a nickel wire provided with gold plating, a wire of titanium alloy or the like having elasticity or shape memory characteristic. Further, it is desirable that the diameter of the wire 21 is in the range of about 0.02 to 0.2 mm.

Figure 2A:
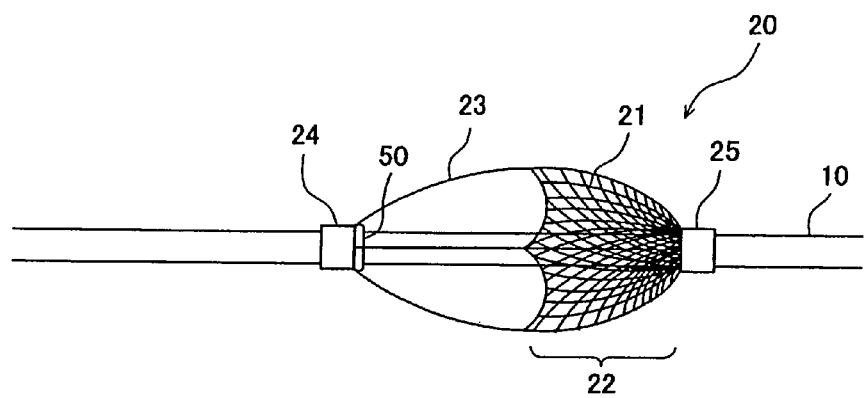
FIG. 2 contains schematic views showing a filter portion of the catheter apparatus of FIG. 1.

FIG. 2 shows the outline of the filter portion 20. As shown in FIG. 2(a), in the normal state, the entire filter portion 20 is substantially elliptical, and has the shape of a parachute in which a net portion 22 is disposed on the distal side, and a support wire 23 for supporting the net portion 22 is disposed on the proximal side. In the net portion 22 corresponding to a canopy of the parachute, the blood is passed through, while it is possible to trap an embolus.

Figure 2B:
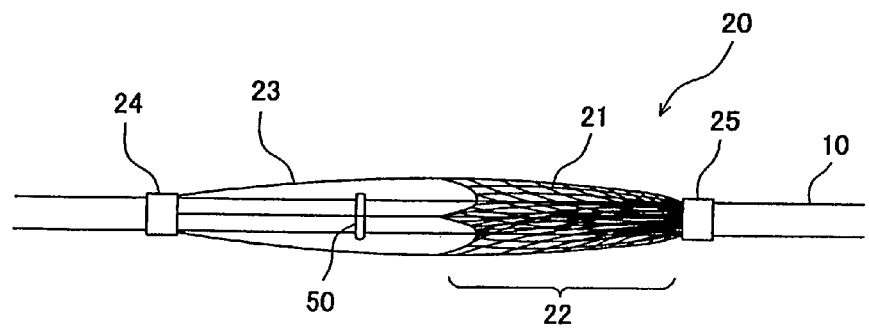

The proximal side of the support wire 23 is tied by a tie portion (proximal side tie portion) 24 in the shape of a ring. The proximal side tie portion 24 is provided to be slidable in the axis direction with respect to the catheter 10. Meanwhile, the distal side of the support wire 23 is tied by a tie portion (distal side tie portion) 25 in the shape of a ring together with the wire 21 constituting the net portion 22. In addition, the distal side tie portion 25 is fixed to the catheter 10. Therefore, the filter portion 20 is capable of forming the expansion state as shown in FIG. 2(a), and the contraction state as shown in FIG. 2(b), by the side tie portion 24 sliding to shift with respect to the fixed distal side tie portion 25.

The filter portion 20 is carried to a lesion area inside the lumen such as the blood vessel with the portion 20 stored inside a carrier catheter together with the catheter 10, as described later. In the state in which the portion 20 is stored inside the carrier catheter, as shown in FIG. 2(b), the filter portion 20 linearly contracts to be thin, and when the portion 20 is retrieved from the carrier catheter, as shown in FIG. 2(a), automatically expands by elasticity or shape memory characteristic, and changes to the shape of a parachute.

In addition, in the above-mentioned description, described as an example is the configuration in which the distal side tie portion 25 of the filter portion 20 is fixed to the catheter 10, and the proximal side tie portion 24 is capable of shifting along the catheter 10, but the fixed side and the shift side of the tie portions may be mutually inverse. Further, both of the tie portions 24, 25 are configured to be able to shift along the catheter 10, and a stopper 50 (protrusion portion) for regulating shifts of both tie portions 24, 25 may be provided between the both tie portions 24, 25. In other words, both of the tie portions 24, 25 are made slidable in the certain range to hit the stopper 50, and the portion thereby expands and contracts in the certain range. Thus, as long as the filter portion 20 is capable of expanding and contracting while being restricted within the certain range, it is possible to adopt any configurations.

Further, in the above-mentioned description, described as an example is the filter portion 20 that expands in the shape of a parachute, but it is possible to apply any other shapes that can trap an embolus.

As well as an introduction opening 31 for dispensing a drug, etc. the liquid introduction portion 30 is provided with a delivery opening 32 to perform blood collection, etc., a switch portion 33 for switching between introduction and delivery, and a tube 34 connected to the branch portion 40.

The introduction opening 31 is coupled to a syringe pump or the like with a drug, etc. to introduce into a lumen such as the blood vessel, and the liquid is fed into the lumen from the opening 31 through the branch portion 40 and catheter 10. Meanwhile, the delivery opening 32 is coupled to a syringe or the like, and by applying a negative pressure, body fluid such as blood is collected from the inside of the lumen such as the blood vessel.

The switch port ion 33 is comprised of a switch valve for switching the function of the catheter apparatus 1 between introduction from the introduction opening 31 to the inside of the lumen and delivery from the inside of the lumen to the delivery opening 32. Further, the tube 34 is a tube to branch from the branch portion 40 to the liquid introduction portion 30.

Figure 3:
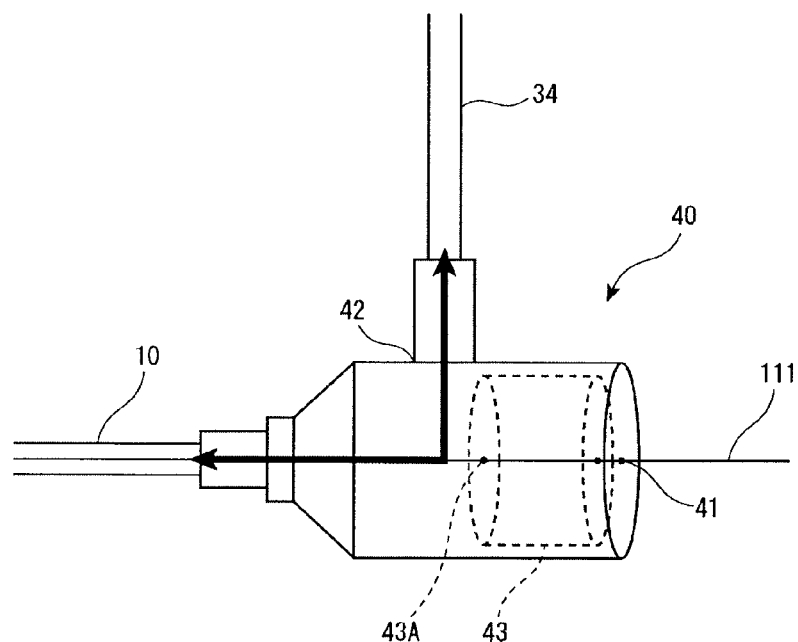
FIG. 3 is a schematic view showing a branch portion of the catheter apparatus of FIG. 1.

The branch portion 40 is a substantially cylindrical member provided in the base end 12 of the catheter 10, and is operated outside the body of a patient together with the liquid introduction portion 30 in the catheter apparatus 1. FIG. 3 shows details of the branch portion 40. The branch portion 40 is provided with a guide wire insertion hole 41 in which a guide wire 111 is inserted, and a connection portion 42 connected to the tube 34 of the liquid introduction portion 30 to communicate to the tube 34 from the catheter 10. Further, inside the portion 40 is provided a seal material (seal means) 43 for preventing the liquid from leaking to the guide wire insertion hole 41, while not preventing circulation between the catheter 10 and the tube 34 of the liquid introduction portion 30.

The seal material 43 is provided with a guide wire insertion hole 43A to insert the guide wire 111. The guide wire 111 is capable of shifting in the axis direction inside the catheter 10 through the guide wire insertion hole 43. In order to prevent leakage of liquid to introduce or deliver as much as possible, the seal member 43 is comprised of an elastic material such as rubber, and the inside diameter of the guide wire insertion hole 43A is determined to be optimal in view of the outside diameter and slipperiness of the guide wire 111, liquid amount of leakage, and the like.

For example, the catheter apparatus 1 as described above is used as described below.

(1) First, as shown in FIG. 4(a), the guide wire 111 is inserted to a position exceeding a lesion area 103 to which an embolus 102 adheres inside a blood vessel 101.

(2) Subsequently, as shown in FIG. 4(b), with the filter portion 20 and catheter 10 stored inside the carrier catheter 121, the guide wire 111 is passed through the center hole of the catheter 10, and along the wire, the carrier catheter 121 is fed into the blood vessel 101. Then, when the filter portion 20 is positioned near the distal side of the lesion area 103, transport is halted.

(3) Next, as shown in FIG. 5(a), only the carrier catheter 121 is withdrawn with respect to the catheter 10, and the filter portion 20 is exposed to the inside of the blood vessel 101. Then, the filter portion 20 expands inside the blood vessel 101. Therefore, blood collection, drug administration and the like are performed by the catheter 10. Further, it is possible to trap an isolated embolus 102A by the filter portion 20.

(4) After the use, as shown in FIG. 5(b), the carrier catheter 121 is moved forward, and the filter portion 20 is stored inside the carrier catheter 121.

(5) Subsequently, the guide wire 111 and carrier catheter 121 are removed from the blood vessel 101, together with the catheter 10 and filter portion 20.

In addition, by combining an embolus cut instrument with the catheter apparatus 1 to use, it is possible to perform cut and trapping of the embolus 102, blood sampling, drug administration, etc. more efficiently. In other words, for example, a coil-shaped embolus cut instrument is passed into the catheter 10, exposed from the front end 11 of the catheter 10, and scrapes off the embolus 102 of the lesion area 103, and it is thus possible to perform blood sampling, drug administration or the like while trapping the cut embolus 102A by the filter portion 20.

In addition, the example of assuming a coronary artery of the heart is described above, but the catheter apparatus is applicable to other general lumens of the human body.

By configuring as described above, according to the catheter apparatus of the invention, it is possible to perform removal of an embolus such as a thrombus, administration of a drug, etc. and sampling of body fluid such as blood at the same time inside a lumen of the human body.

The Embodiment of the invention is described as mentioned above, but the invention is not limited to the above-mentioned Embodiment, is capable of being modified in various manners based on the subject matter of the invention, and is not intended to exclude the modifications from the scope of the invention.

INDUSTRIAL APPLICABILITY

The invention relates to a catheter apparatus capable of trapping emboli such as thrombi, while at the same performing administration of a drug, etc. and sampling of body fluid such as blood inside a lumen of the human body, and has industrial applicability.

REFERENCE SIGNS LIST

1 Catheter apparatus
10 Catheter
11 Front end
12 Base end
20 Filter portion (embolus trapping means)
21 Wire
22 Net portion
23 Support wire
24 Proximal side tie portion
25 Distal side tie portion
30 Liquid introduction portion
31 Introduction opening
32 Delivery opening
33 Switch portion
34 Tube
40 Branch portion
41 Guide wire insertion hole
42 Connection portion
43 Seal material (seal means)
43A Guide wire insertion hole

The invention claimed is:

1. A catheter apparatus, comprising:
a catheter that is adapted to be inserted into a lumen of a human body, the catheter having a center hole extending from a front end portion to a base end portion thereof for passing therethrough a guide wire when inserting the catheter into the lumen of the human body;
an embolus trapping part adapted to trap an embolus inside the lumen of the human body, provided on an outer surface near the front end portion of the catheter, the embolus trapping part including:
  a net member including a weaved elastic or shape memory wire material having a net shape, and
  proximal side and distal side tie portions each being disposed respectively on a proximal end and a distal end of the wire material, for tying the proximal and distal ends of the wire material to the outer surface of the catheter;
a carrier catheter to carry the catheter and the embolus trapping part stored therein to a lesion area inside the lumen of the human body and to retrieve the catheter and the embolus trapping part stored therein from the lesion area;
a liquid introducing portion for introducing a liquid including a drug solution into the catheter, and including:
  a tube communicating with the catheter,
  an introduction opening for introducing the liquid into the catheter through the tube,
  a delivery opening adapted to deliver body fluid collected from the center hole at the front end portion of the catheter through the catheter and the tube, and
  a switch portion for selectively switching a connection between the tube and the introduction opening or the delivery opening; and
a branch portion which is connected to the base end portion of the catheter and the tube of the liquid introducing portion, and is provided with:

an insertion hole communicating to the center hole at the base end portion of the catheter and adapted to pass only the guide wire, a connection portion connecting and communicating the tube to the center hole at the base end portion of the catheter for introducing the liquid into and delivering the body fluid from the lumen of the human body through the center hole, and a seal member disposed in the branch portion, for preventing the liquid supplied from the tube through the catheter to the lumen of human body, or the body fluid collected from the lumen of the human body to the tube through the catheter from leaking from the insertion hole to outside of the branch portion;

wherein the embolus trapping part is structured so that at least one of the proximal side tie portion or the distal side tie portion shifts along the catheter to reduce or increase a distance between the proximal and distal side tie portions to open and close the net member, and when the carrier catheter is moved rearward in relation to the catheter so that the net member is released from a front end of the carrier catheter into the lumen of the human body, the net member expands from the outer surface of the catheter to trap the embolus, and when the carrier catheter is moved forward in relation to the catheter so that the net member is retrieved into the carrier catheter from the front end thereof, the net member is retracted to the outer surface of the catheter to be stored into the carrier catheter, and the seal member includes a guide wire insertion hole adapted to pass only the guide wire therethrough.

2. The catheter apparatus according to claim 1, wherein the net member opens and closes in a shape of a parachute.

3. The catheter apparatus according to claim 1, wherein the wire material is formed from a nickel titanium wire, a titanium wire, a wire of complex material of a wire made of platinum or gold and nickel titanium alloy, a nickel wire provided with gold plating, or a wire of titanium alloy.

4. The catheter apparatus according to claim 1, wherein when the catheter and the delivery opening are communicated with each other through the switch portion, by applying a negative pressure to the delivery opening, the body fluid including blood is extracted from the delivery opening to outside of the liquid introducing portion.

5. The catheter apparatus according to claim 1, wherein the embolus trapping part is inserted into the lesion area in the lumen with the catheter while the embolus trapping part is contracted and stored in the carrier catheter, and the embolus trapping part expands as the carrier catheter separates from the embolus trapping part.

6. The catheter apparatus according to claim 1, wherein the catheter comprises an embolus cut instrument cutting the embolus, exposed through a tip of the catheter, and the embolus trapping part traps the embolus cut by the embolus cut instrument.

7. The catheter apparatus according to claim 1, wherein the embolus trapping part further comprises a stopper provided on the outer surface of the catheter between the proximal side and distal side tie portions to restrict shifting of the proximal side and distal side tie portions to a predetermined range along the catheter.

8. The catheter apparatus according to claim 7, wherein the catheter is one and is structured so that one of the proximal side or distal side tie portion of the embolus trapping part is fixedly connected to the outer surface of the one catheter, and another of the proximal side or distal side tie portion is slidably connected to the outer surface of the one catheter.

9. The catheter apparatus according to claim 8, wherein said another of the proximal side or distal side tie portion of the embolus trapping part is disposed on a front end side of the one catheter.

10. The catheter apparatus according to claim 8, wherein the proximal side and distal side tie portions of the embolus trapping part have a ring shape so that the proximal side tie portion is slidably disposed on the outer surface of the one catheter in an axis direction of the one catheter, and the distal side tie portion is fixed to the outer surface of the one catheter.

11. The catheter apparatus according to claim 10, wherein the one catheter extends through the embolus trapping part so that the proximal side and distal side tie portions of the embolus trapping part are arranged between the front end portion and the base end portion of the one catheter.

12. The catheter apparatus according to claim 11, wherein the one catheter is structured so that the liquid from the introducing opening of the liquid introducing portion is supplied to the center hole at the front end portion of the one catheter.

13. The catheter apparatus according to claim 1, wherein the embolus trapping part further comprises a support wire for supporting the net member so that the net member is disposed on the distal side tie portion in respect to the proximal side tie portion, the net member includes an open portion connected to the proximal side tie portion through the support wire and opened to the front end portion of the catheter for allowing the embolus to enter the net member, and a closed portion connected to the catheter through the distal side tie portion for trapping the embolus entering from the open portion, and the embolus trapping part is structured so that when the carrier catheter is withdrawn to release the net member from the front end of the carrier catheter, the proximal side tie portion slides toward the distal side tie portion to expand the net member and trap the embolus, and when the carrier catheter is moved toward the net member to retrieve the net member, the proximal side tie portion slides away from the distal side tie portion to retain the net member inside the carrier catheter.

* * * * *